United States Patent [19]
Paris et al.

[11] 4,183,934
[45] Jan. 15, 1980

[54] 4-HYDROXY-7-(SUBSTITUTED)PHENYLP-TERIDINES

[75] Inventors: Gerard Y. Paris, Duvernay; Denis G. Cimon, Montreal-Nord; Dilbagh S. Bariana, Pointe-Claire; Anthony Fung, Pierrefonds, all of Canada

[73] Assignee: Abbott Laboratories, North Chicago, Ill.

[21] Appl. No.: 951,936

[22] Filed: Oct. 16, 1978

[51] Int. Cl.² .................. A61K 31/505; C07D 475/02
[52] U.S. Cl. .................................... 424/251; 544/257
[58] Field of Search ........................ 544/257; 424/251

[56] References Cited
PUBLICATIONS

Weinstock et al., *J. Med. Chem.*, 1968, 11(3), pp. 573–579.

*Primary Examiner*—Paul M. Coughlan, Jr.
*Attorney, Agent, or Firm*—Paul D. Burgauer; Robert L. Niblack

[57] ABSTRACT

Specific 4-hydroxy-pteridines carrying particular phenyl substituents in the 7-position and no substituents in the 2-position have been found to be excellent non-kaliuretic diuretics at doses of 30 to 500 mg/kg in warm-blooded animals.

16 Claims, No Drawings

4-HYDROXY-7-(SUBSTITUTED)PHENYLPTERIDINES

DETAILED DESCRIPTION OF THE INVENTION

Pteridines have been known for several decades and some particular pteridines have been suggested or used as antimalarial or antibacterial drugs. All active pteridines reported carry substituents in the 2-position.

It has been found that 4-hydroxy-7-phenylpteridine and phenyl-substituted derivatives thereof carrying only position-specified substituents in the phenyl ring have excellent diuretic activity with the highly desirable advantage of closely maintaining the normal potassium level. The compounds of the present invention are best described by reference to formula I

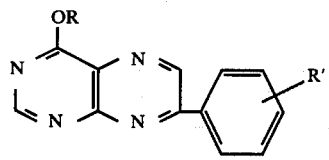

wherein R is hydrogen or methyl and wherein R' is chlorine; hydrogen, loweralkyl, carboxy, loweralkylamino or diloweralkylamino or pharmaceutically acceptable acid addition salts thereof. These compounds have nonkaliuretic diuretic activity at oral doses of 30 to 500 mg/kg or approximately 20%-100% of these amounts by intramuscular or subcutaneous administration. The diuretic effect of these compounds is totally unexpected when considered in the light of the complete lack of diuretic activity of very closely resembling structures, e.g., the 2,4-diamino-7-phenylpteridine.

The compounds of the present invention are made by condensing 4,5-diamino-6-hydroxy-(or 6-methoxy)-pyrimidine sulfate in a hot aqueous medium with the appropriately ring-substituted phenylglyoxal. The reaction usually is instantaneous, and the pteridine formed precipitates. To optimize the yield, the mixture is best stirred for 30 minutes at a temperature between room temperature and the boiling point of the mixture. Before removal of the pteridine, it is advantageous to lower the temperature of the condensation mixture to 0–5 degrees C.

In order to illustrate the procedure for making the compounds of the present invention, reference is made to the following examples which, however, are not intended to limit the invention in any way.

EXAMPLE 1

4-Hydroxy-7-Phenylpteridine

To a hot solution of 4.8 g. of sodium acetate in 30 ml. of water was added 2.25 g. of 4,5-diamino-6-hydroxy pyrimidine sulfate. While stirring, 2.28 g. of phenylglyoxal monohydrate in 10 ml. of hot ethanol was added at once. A precipitate formed immediately. The mixture was stirred for 30 minutes at room temperature, cooled to 0 degrees C. and filtered. The solids collected were washed with 200 ml. of water, 100 ml. of acetone and finally with 100 ml. of ether to produce a dry yield of 1.9 g. (85% of theory) of 4-hydroxy-7-phenylpteridine. The compound was recrystallized from DMSO/water; its melting point was above 325 degrees C. Mass spectrum m/e calculated is 224; found: 224.

Oral administration of this compound at a dose of 100 mg/kg to 8 rats increases the mean 2-hour sodium excretion from 2.43 to 5.27 meq/kg; the corresponding values for potassium are 1.64 to 1.94 and for chlorine 2.48 to 4.58. Urine volume increases from 21.31 to 44.95 ml/kg. In all measurements given above, the first numbers indicate those of the control group with both control and test groups receiving 50 ml. per kg. of body weight of 0.9% saline and the drug vehicle, said vehicle being a 0.5% aqueous methylcellulose solution, at a rate of 2 ml/kg of body weight. The control group showed a Na/K excretion ratio of 1.46 while the drug test group showed this ratio at 2.74.

The cumulative 6-hour Na/K ratios are 1.65 for the control group (38.44 ml/kg urine volume) and 2.37 for the test group (73.44 ml/kg). Sodium, potassium and chlorine values (with controls) are 8.98 (4.98), 3.87 (2.98), 7.85 (4.88) meq/kg.

At a test dose of 30 mg/kg, the 0-2 hour test group results are 25.06 ml/kg (10.93) of urine, 3.90 meq/kg (1.87) of Na, 1.96 meq/kg (1.32) of K, 4.10 meq/kg (2.36) of Cl, with a Na/K ratio of 2.01 (1.39 for the control group). The corresponding 0-6 hour values are 40.69 ml/kg (28.53) urine volume, 6.90 meq/kg (5.19) of Na, 3.60 meq/kg (2.98) of K, 6.72 meq/kg (5.38) Cl and a 1.95 Na/K ratio (control 1.75); the 0-24 hours test figures for urine were 67.00 ml/kg (60.83); for Na 9.67 (9.23), for K 6.26 (5.72) and for Cl 8.97 (8.35) meq/kg with a ratio of 1.59 (control 1.73).

At doses of 10 mg/kg, respectively, the Na/K ratios were 2.10 (1.39) after 2 hours, 2.35 (1.75) after 6 hours and 1.84 (1.73) after 24 hours.

EXAMPLE 2

4-Methoxy-7-Phenylpteridine

To a solution of 0.5 g. of metallic sodium in 50 ml. of methanol was added 1.9 g. of 4-amino-6-chloro-5-nitropyrimidine. The reaction mixture was refluxed for 90 minutes and then cooled. The precipitated solid was filtered, washed successively with 50 ml. of water, 30 ml. of methanol and 30 ml. of ether to yield 1.6 g. (86%) of 4-amino-6-methoxy-5-nitropyrimidine.

A suspension of 4.8 g. of this compound in 200 ml. of methanol was hydrogenated over 0.5 g. of Raney nickel at room temperature and atmospheric pressure until 2 liters of hydrogen was absorbed. The mixture was filtered and the filtrate evaporated to dryness to yield crude 4,5-diamino-6-methoxypyrimidine which was used without further purification.

Of the above, 3.95 g. was dissolved in 80 ml. of water containing 4.8 ml. of concentrated HCl. After adding 13.4 g. of sodium acetate, the solution was heated to 50 degrees C. and a solution of 6.35 g. of phenylglyoxal monohydrate in 30 ml. of ethanol was added. Work-up of the precipitate was carried out as in Example 1 to yield 5.6 g. of crude 4-methoxy-7-phenylpteridine. After two recrystallizations from DMSO, 1.9 g. (28%) of the pure compound was obtained; melting point: 205-7 degrees C.

Testing of this compound at an oral dose of 100 mg/kg in accordance with the procedure of Example 1 gave the results shown in Table I.

Table I

| | Control | | Compound | |
|---|---|---|---|---|
| | 0-2 hrs. | 0-6 hrs. | 0-2 hrs. | 0-6 hrs. |
| Urine vol. | 6.32 | 23.22 | 24.14 | 51.53 ml/kg |
| Sodium | 1.03 | 3.60 | 3.08 | 7.12 meq/kg |
| Potassium | 0.70 | 1.89 | 1.24 | 2.51 meq/kg |
| Chloride | 1.24 | 4.09 | 3.19 | 6.45 meq/kg |
| Na/K ratio | 1.43 | 1.90 | 2.64 | 2.99 |

EXAMPLE 3

4-Hydroxy-7-(4-N,N-Dimethylaminophenyl)Pteridine

To a composition of 5.2 g. of selenous acid in 40 ml. of dioxane was added 3.27 g. of 4-(N,N-dimethylamino)acetophenone. After refluxing the mixture for four hours, it was filtered and the filtrate was evaporated. A hot suspension of 3.9 g. of this glyoxal in 15 ml. of ethanol was added to a stirred suspension of 4.5 diamino-6-hydroxypyrimidine sulfate. Stirring was continued overnight and the pteridine was isolated as in Example 1.

The crude solid was purified by refluxing 30 minutes in 250 ml. 2N NaOH, acidifying with HCl to pH 4, filtration and drying. Cyrstallization from DMSO gave 1.0 g. (28%) of 4-hydroxy-7-(4-N,N-dimethylaminophenyl)pteridine, melting point 250 degrees C., with a mass spectrum of 267 (calcd: 267).

Testing of this compound in accordance with Example 1 at 100 mg/kg (oral) gave the results shown in Table II.

Table II

| | Control | | Compound | |
|---|---|---|---|---|
| | 0-2 hrs. | 0-6 hrs. | 0-2 hrs. | 0-6 hrs. |
| Urine vol. | 11.06 | 28.69 | 17.45 | 58.60 ml/kg |
| Na | 1.50 | 4.21 | 1.58 | 6.05 meq/kg |
| K | 0.79 | 1.77 | 0.79 | 2.05 meq/kg |
| Cl | 1.88 | 5.00 | 1.96 | 7.56 meq/kg |
| Na/K ratio | 1.81 | 2.41 | 2.00 | 2.95 |

EXAMPLE 4

4-Hydroxy-7-(4-Chlorophenyl)Pteridine

In accordance with Example 1, 3.03 g. of the substituted pyrimidine sulfate was condensed with 3:73 g. of 4-chlorophenylglyoxal to produce 1.95 g. (56%) of 4-hydroxy-7-(4-chlorophenyl)pteridine. The test results obtained in the described manner with a 100 mg/kg oral dose in rats produced the results shown in Table III.

Table III

| | Control | | Drug | |
|---|---|---|---|---|
| | 0-2 hrs. | 0-6 hrs. | 0-2 hrs. | 0-6 hrs. |
| Urine vol. | 15.61 | 32.74 | 19.61 | 47.60 ml/kg |
| Na | 2.18 | 3.88 | 2.53 | 6.20 meq/kg |
| K | 1.42 | 2.34 | 1.46 | 3.14 meq/kg |
| Cl | 2.64 | 4.48 | 3.02 | 6.62 meq/kg |
| Na/K ratio | 1.58 | 2.26 | 1.73 | 1.97 |

EXAMPLE 5

4-Hydroxy-7-(3-Chlorophenyl)Pteridine

By replacing the 4-chlorophenyl glyoxal of Example 4 with the 3-chloro-analog, 2.25 g. of 4-hydroxy-7-(3-chlorophenyl)pteridine was obtained; melting point >315 degrees C. The test results after 100 mg/kg oral administration are shown in Table IV.

Table IV

| | Control | | Drug | |
|---|---|---|---|---|
| | 0-2 hrs. | 0-6 hrs. | 0-2 hrs. | 0-6 hrs. |
| Urine vol. | 10.42 | 26.01 | 15.26 | 29.42 ml/kg |
| Na | 1.27 | 3.28 | 1.75 | 3.73 meq/kg |
| K | 0.79 | 1.64 | 0.95 | 1.77 meq/kg |
| Cl | 1.56 | 4.03 | 1.97 | 4.32 meq/kg |
| Na/K ratio | 1.57 | 2.00 | 1.84 | 2.14 |

EXAMPLE 6

4-Hydroxy-7-(4-Carboxyphenyl)Pteridine

Oxidation of 4-acetylbenzoic acid with selenous acid and subsequent condensation of 5.85 g. of this aldehyde with 4.56 g. of 4,5-diamino-6-hydroxypyrimidine sulfate as shown in Example 1 produced 2.5 g. of 4-hydroxy-7-(4-carboxyphenyl)pteridine; melting point >300 degrees. The results after 100 mg/kg oral administration are shown in Table V.

Table V

| | Control | | Drug | |
|---|---|---|---|---|
| | 0-2 hrs. | 0-6 hrs. | 0-2 hrs. | 0-6 hrs. |
| Urine vol. | 6.88 | 22.04 | 11.43 | 28.42 ml/kg |
| Na | 1.04 | 3.16 | 1.40 | 3.85 meq/kg |
| K | 0.77 | 1.67 | 0.82 | 1.73 meq/kg |
| Cl | 1.28 | 3.78 | 1.48 | 4.10 meq/kg |
| Na/K ratio | 1.47 | 1.99 | 1.71 | 2.22 |

EXAMPLE 7

4-Hydroxy-7-(3-tolyl)Pteridine

A solution of 3.6 g. of 3-tolylglyoxal in 15 ml. of ethanol was added to a stirred suspension of 3.26 g. of 6-hydroxy-4,5-diaminopyrimidine sulfate in 30 ml. of hot water containing 6.45 g. of sodium acetate. Stirring was continued for 17 hours at room temperature and the formed precipitate was then filtered, washed twice each with methanol and ether to yield 2.7 (28%) of 4-hydroxy-7-(3-tolyl)pteridine. Recrystallization from DMSO/water produced the pure product; melting point 248-50 degrees C. The test results (100 mg/kg; oral) are shown in Table VI.

Table VI

| | Control | | Drug | |
|---|---|---|---|---|
| | 0-2 hrs. | 0-6 hrs. | 0-2 hrs. | 0-6 hrs. |
| Urine vol. | 10.90 | 27.84 | 17.62 | 30.61 ml/kg |
| Na | 1.53 | 4.00 | 1.87 | 3.64 meq/kg |
| K | 0.87 | 2.10 | 0.82 | 1.45 meq/kg |
| Cl | 1.72 | 4.60 | 2.05 | 3.94 meq/kg |
| Na/K ratio | 1.77 | 1.97 | 2.30 | 2.54 |

The compounds of the present invention are preferably used in oral dosage forms such as tablets, capsules, wafers, elixirs, syrups and the like. For liquid forms, the above compounds are suspended in an aqueous medium containing the customary flavoring and coloring agents. Since these compounds are essentially insoluble in water, dispersing and/or suspending agents acceptable for human consumption are used together with suspension stabilizers. For the various solid dosage forms, the usual solid diluents are used where required. Capsules can be filled with undiluted powdered or granulated crystals of the new compounds. For tablets, the following standard procedure may be used:

About one-half of 52 g. of cornstarch is milled together with 100 g. of the new drug and 220 g. of calcium phosphate dibasic dihydrate. This blend is milled until homogenous and passed through a 40-mesh screen. The remaining portion of the cornstarch is granulated with water, heated and mixed with the above drug blend in a hot air oven at 50 degrees C. and sifted through a 16-mesh screen. These granules are then mixed with 16 g. of talcum powder, 4 g. of magnesium stearate and 0.8 g. of combined coloring and flavoring additives. The mixture is blended to homogeneity, passed through a 30-mesh screen and blended for another 15 minutes. This blend is compressed into tablets weighing approximately 400 mg. using a 9/32" standard convex punch resulting in tablets of a hardness of 7-9 with each tablet containing 100 mg. of the drug. In a similar fashion, tablets weighing 650 mg. containing 250 mg. of drug can be prepared, preferably in a tableting machine producing bisected tablets.

The compounds of the present invention exhibit no toxic symptons. An oral LD$_{50}$ could not be established as the test animals show no changes at doses of up to 2 g/kg. This phenomenon is probably based on the low solubility of the drugs which makes it even more surprising that such a pronounced, nonkaliuretic diuretic effect is obtained at doses of 30 mg/kg and above. A practical range for daily oral administration is between 30 and 500 mg/kg with a preferred range being 50-250 mg/kg.

What is claimed is:

1. A compound of the formula

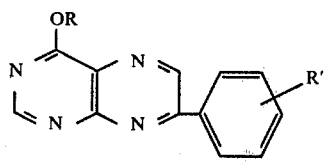

wherein R is hydrogen or methyl and wherein R' is hydrogen, chlorine, carboxy, loweralkylamino, diloweralkylamino or loweralkyl, or a pharmaceutically acceptable acid addition salt thereof.

2. The compound of claim 1 wherein R is hydrogen and R' is chlorine.

3. The compound of claim 2 wherein said chlorine is in the p-position.

4. The compound of claim 1 wherein R is hydrogen and R' is loweralkyl.

5. The compound of claim 4 wherein said loweralkyl is a methyl group in the m-position.

6. The compound of claim 1 wherein said diloweralkylamino is dimethylamino and R is hydrogen.

7. A medicinal composition for increasing the excretion of sodium and chlorine ions from warm-blooded animals containing a compound of the formula:

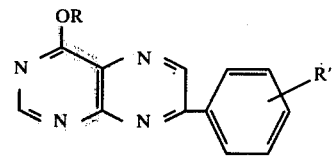

wherein R is hydrogen or methyl and R' is hydrogen, chlorine, carboxy, loweralkylamino, diloweralkylamino or loweralkyl, or a pharmaceutically acceptable acid addition salt thereof.

8. A composition of claim 7 in the form of a medicinal tablet for oral administration.

9. The composition of claim 7 in the form of a sterile liquid suitable for intramuscular or intravenous injection.

10. The method of increasing urine excretion in a warm-blooded animal consisting essentially in administering to said animal a diuretically sufficient amount of a compound of the formula:

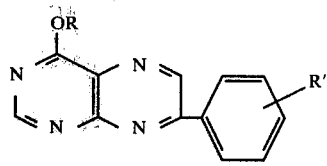

wherein R is hydrogen or methyl and R' is hydrogen, chlorine, loweralkylamino, diloweralkylamino or loweralkyl, or a pharmaceutically acceptable acid addition salt thereof.

11. The method of claim 10 wherein said amount is between 30 and 500 mg/kg/day.

12. The method of claim 11 wherein R is hydrogen and R' is chlorine.

13. The method of claim 12 wherein said chlorine is in the p-position.

14. The method of claim 11 wherein R is hydrogen and R' is loweralkyl.

15. The method of claim 14 wherein said loweralkyl is a methyl group in the m-position.

16. The method of claim 11 wherein said diloweralkylamino is dimethylamino and R is hydrogen.

* * * * *